(12) United States Patent
Strnad et al.

(10) Patent No.: US 11,371,920 B2
(45) Date of Patent: Jun. 28, 2022

(54) SAMPLE CONTAINER AND USE OF A SAMPLE CONTAINER

(71) Applicant: Testo SE & Co. KGaA, Lenzkirch (DE)

(72) Inventors: Martin Strnad, Simonswald (DE); Andreas Schnur, Rottweil (DE); Joel Riemer, Breitnau (DE); Oliver Wiech, Donaueschingen (DE)

(73) Assignee: Testo SE & Co. KGaA, Lenzkirch (DE)

( * ) Notice: Subject to any disclaimer, the term of this patent is extended or adjusted under 35 U.S.C. 154(b) by 0 days.

(21) Appl. No.: 16/911,594

(22) Filed: Jun. 25, 2020

(65) Prior Publication Data
US 2020/0408654 A1 Dec. 31, 2020

(30) Foreign Application Priority Data
Jun. 27, 2019 (DE) .......................... 102019117411.2

(51) Int. Cl.
*G01N 1/44* (2006.01)

(52) U.S. Cl.
CPC ..................... *G01N 1/44* (2013.01)

(58) Field of Classification Search
CPC ......... B01L 2200/025; B01L 2200/026; B01L 2200/141; B01L 2300/042; B01L 2300/0825; B01L 2300/0858; B01L 2400/0683; B01L 3/50825; C12M 23/34; G01N 1/44
See application file for complete search history.

(56) References Cited

U.S. PATENT DOCUMENTS

| | | | | |
|---|---|---|---|---|
| 5,458,252 | A * | 10/1995 | Logel | B65D 43/0231 220/240 |
| 5,955,675 | A | 9/1999 | Peterson | |
| 2002/0127147 | A1* | 9/2002 | Kacian | B01L 3/565 422/570 |
| 2006/0029517 | A1 | 2/2006 | Hartselle | |
| 2011/0250106 | A1* | 10/2011 | Lafond | A61B 10/0096 422/551 |
| 2011/0250586 | A1* | 10/2011 | Halverson | B01L 3/5021 435/5 |

(Continued)

FOREIGN PATENT DOCUMENTS

| | | |
|---|---|---|
| DE | 69732688 | 7/2005 |
| EP | 0569835 | 11/1993 |
| EP | 2191896 | 6/2010 |

*Primary Examiner* — Francis C Gray
(74) *Attorney, Agent, or Firm* — Volpe Koenig

(57) ABSTRACT

A sample container (1) with a sample-receiving chamber (2) and with a closure piece (3) for closing the sample-receiving chamber (2) in a sealed manner. The sample container (1) has at least two seals (4, 5, 15, 16) arranged separately from each other, and/or the sample-receiving chamber (2) is subdivided into at least two compartments (6) which are thermally decoupled from each other and are connectable by liquid, and/or the sample container (1) has, on an outer wall (7) of the sample-receiving chamber (2), at least one coupling point (8) for the docking of an auxiliary container (9) via a matching counter-coupling point (10) of the auxiliary container (9). The outer wall (7) has at least one predetermined breaking point (11), which is pierced through upon coupling to the auxiliary container (9).

17 Claims, 6 Drawing Sheets

(56) References Cited

U.S. PATENT DOCUMENTS

| | | | |
|---|---|---|---|
| 2014/0046215 A1* | 2/2014 | Hu | A61B 10/007 |
| | | | 600/584 |
| 2014/0096598 A1* | 4/2014 | Halverson | G01N 15/04 |
| | | | 73/61.72 |
| 2014/0106397 A1* | 4/2014 | Rajagopal | G01N 1/4077 |
| | | | 435/287.1 |
| 2017/0106365 A1* | 4/2017 | Berner | B01L 3/50825 |
| 2017/0333893 A1* | 11/2017 | Ziegler | B65D 43/0225 |
| 2017/0336400 A1* | 11/2017 | Meng | G01N 33/54366 |
| 2019/0083975 A1* | 3/2019 | Mitra | C12Q 1/6844 |

* cited by examiner

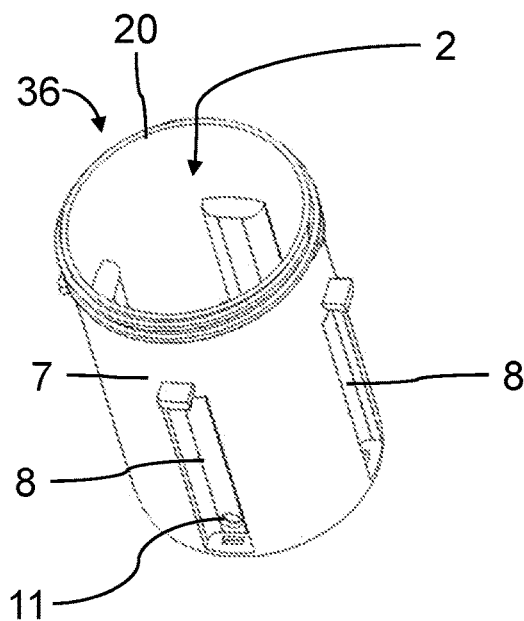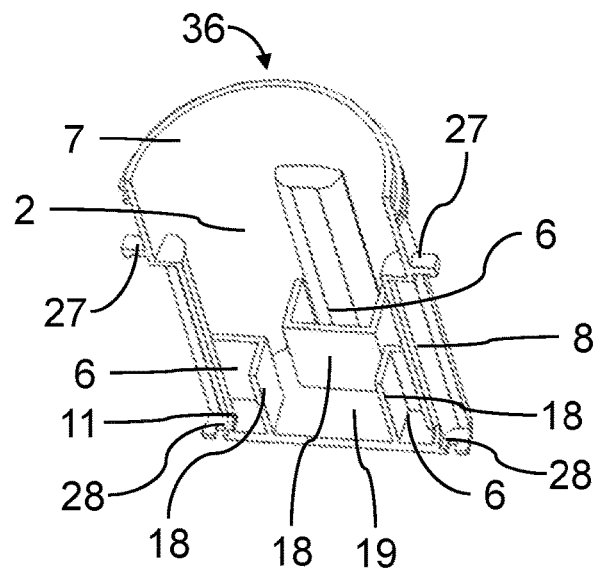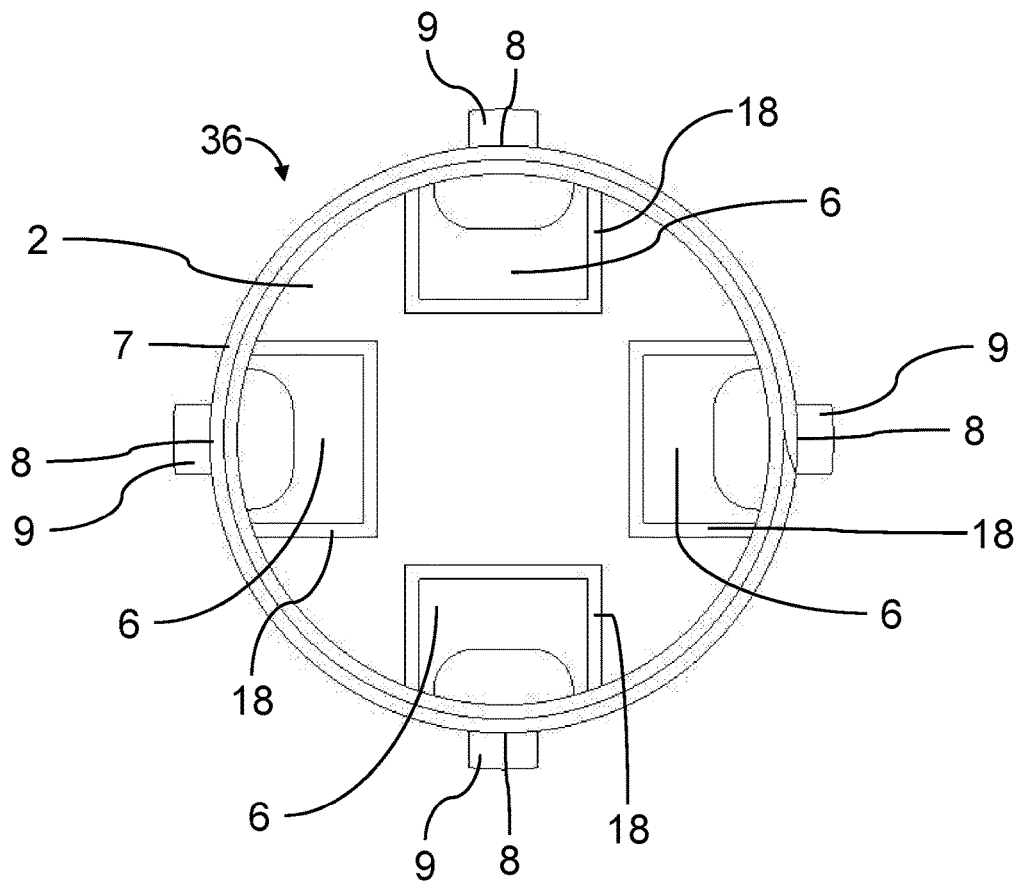
Fig. 5    Fig. 6
Fig. 7

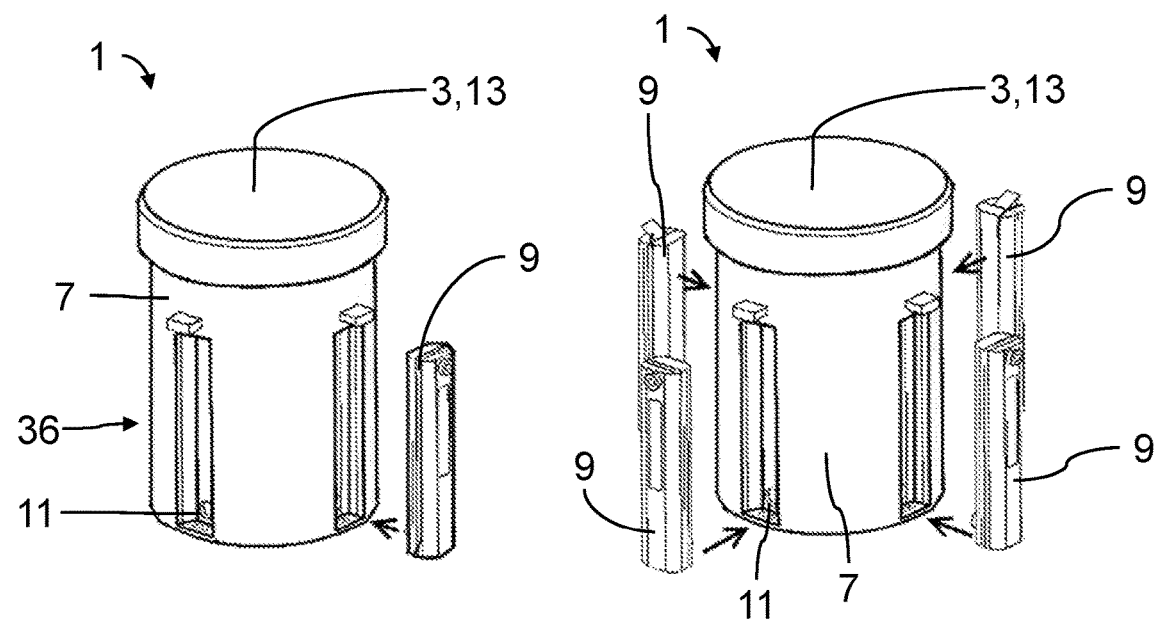
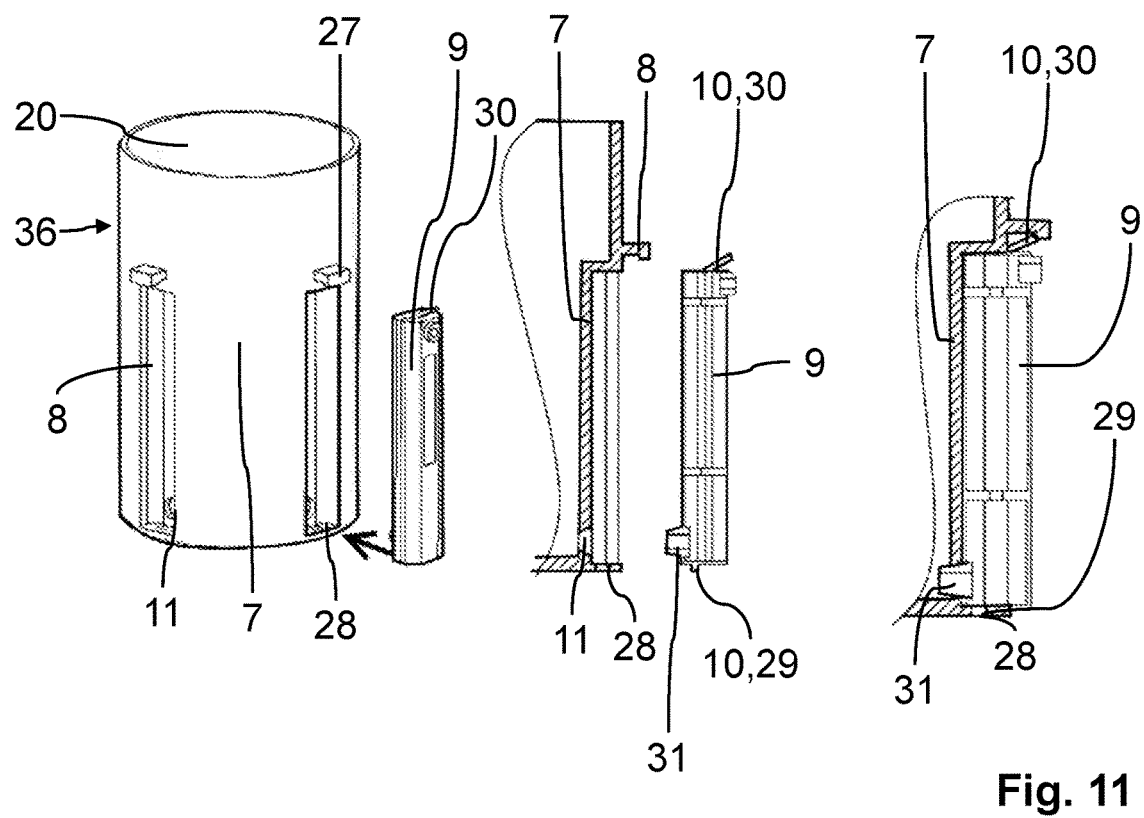
Fig. 10
Fig. 11

SAMPLE CONTAINER AND USE OF A SAMPLE CONTAINER

INCORPORATION BY REFERENCE

The following documents are incorporated herein by reference as if fully set forth: German Patent application No. DE 102019117411.2, filed Jun. 27, 2019.

TECHNICAL FIELD

The invention relates to a sample container with a sample-receiving chamber and with a closure piece for closing the sample-receiving chamber, wherein the sample container may be suitable, for example, for cultivating microorganisms and/or for performing a chemical reaction. In particular, the sample container may be suitable for cultivating and/or analysis, in particular for chemical analysis, of a sample.

BACKGROUND

Sample containers of the aforementioned type are already known in a large number of different design variants. For example, cell culture dishes, cell culture flasks and microtiter plates are already known which are used in the cultivation of animal or plant cells in a nutrient medium. The sample-receiving chambers of these known sample containers are usually individually charged with a sample that is to be cultivated and/or analyzed, which can be a time-consuming process if a large number of different analyses are to be performed. In order to create ideal growth conditions for microorganisms or ideal reaction conditions, the sample containers are often incubated in incubators over a certain period of time.

After carrying out an analysis of a sample treated in a sample container, it is generally necessary for the sample to be inactivated, since the samples often pose a risk to health. Generally speaking, biological samples in particular are killed off by thermal treatment in a positive pressure range, for example in an autoclave.

It is true that a large number of sample containers are already known. However, they have the disadvantage either that they can only be closed without sealing, or that a higher internal pressure develops in the sample container and causes the sample container to open and the sample material to escape.

A further disadvantage of known sample containers is that, in the case of known sample containers having multiple sample-receiving chambers, for example in the case of microtiter plates, the samples contained in the different sample-receiving chambers cannot be treated by different temperatures.

Moreover, when performing cultivation and/or analysis of sample material using known sample containers, it is generally necessary that these operations are carried out by trained personnel. The samples to be cultivated and/or analyzed can pose risks to health. Therefore, if contamination occurs on account of incorrect or unclean handling of the samples, said contamination may be spread by the personnel. It is therefore generally necessary that such critical samples are processed only in closed laboratories and by trained laboratory workers. On account of the highly complex work steps involved in the whole process of cultivation, analysis and inactivation, there is a high risk of contamination of the environment and of the persons present there. It is therefore desirable to make available a sample container with which the risk of contamination of the environment and of the persons present there is reduced or even eliminated.

SUMMARY

The object is therefore to make available a sample container of the type mentioned at the outset, with which at least some of the aforementioned disadvantages are eliminated and of which the use properties are thus improved in relation to known sample containers.

These object/objects is/are achieved by a sample container having one or more features of the invention as described in detail below.

In particular, in order to achieve the object according to the invention, a sample container of the type mentioned at the outset is proposed wherein the sample-receiving chamber can be closed in an airtight manner by means of the closure piece, and wherein the sample container has at least one seal which self-reinforces as the internal pressure increases. In particular, the sample-receiving chamber can be closed in a pressure-tight manner by the closure piece. It is thus possible that, even when exposed to great heat, for example in an autoclave with hot saturated vapor at 121° C., the sample container withstands the internal pressure and/or external pressure acting on the sample container and remains closed. As a result of the seal self-reinforcing as the internal pressure increases, an important safety criterion can be met, namely that a liquid contained in the sample container and undergoing thermal treatment cannot expand to such an extent that the sample escapes and finally contaminates the environment.

In particular, in order to further achieve the object according to the invention, a sample container of the type mentioned at the outset is proposed wherein the aforementioned sample-receiving chamber is subdivided into at least two compartments which are thermally decoupled from each other and are connectable by liquid or which, in the position of use, are connected by liquid. This has the advantage of being able to permit a different thermal treatment of sample material that is provided in a sample container (sequential heating), in particular sample material provided in a sample-receiving chamber. It has hitherto been necessary to store samples in separate sample containers in order to subject them to different thermal treatments. It is thus possible to achieve much simpler handling of the samples and much simpler cultivation and/or analysis of a sample.

In particular, in order to further achieve the object according to the invention, a sample container of the type mentioned at the outset is proposed wherein the sample container has, on an outer wall of the aforementioned sample-receiving chamber, at least one coupling point at which, in order to permit a liquid transfer, an auxiliary container is docked via a matching counter-coupling point. In particular, the outer wall can have at least one predetermined breaking point, which is configured to be pierced through upon coupling to the auxiliary container. This has the advantage that a connection, in particular a liquid connection, is thus easily produced between the sample-receiving chamber and the auxiliary container via a through-opening that is created at the predetermined breaking point. It may be particularly advantageous if the connection between the sample-receiving chamber and the auxiliary container can be made airtight, in particular pressure-tight, or is airtight, in particular pressure-tight, in the position of use. By the coupling of auxiliary container and sample container, a simple analysis of a sample contained in the sample-receiving chamber is possible for example, in particular without the sample-receiving chamber having to be opened while an analysis method is being carried out. By way of the through-opening, an access to the sample container is created, such that an analysis substance from the auxiliary container can come into contact with the sample. The analysis is thus made much simpler. For example, the auxiliary container can have a lateral flow test, particularly in the form of a test strip and/or a lateral flow device. By the coupling of the sample container to the auxiliary container, liquid can flow from the sample-receiving chamber into the auxiliary container, such that an analysis can be carried out. Before the liquid connection is established, an overpressure can be present inside the sample container and/or an underpressure can be present inside the auxiliary container. Thus, after the coupling has been established, a flow of liquid into the auxiliary container is made easier.

Alternatively or in addition to this, the auxiliary container can also contain a substance which can be introduced into the sample-receiving chamber via the above-described liquid connection, by means of the auxiliary container being connected to the sample-receiving chamber. Preferably, before a coupling is established, an overpressure can be provided inside the auxiliary container, which makes it easier for liquid to flow from the auxiliary container into the sample-receiving chamber.

The sample-receiving chamber can be formed, for example, by a beaker. The beaker can have a cylindrical form in particular. The sample-receiving chamber can preferably be produced from a plastic, in particular a non-elastic plastic.

Advantageous embodiments of the invention are described below and may be used alone or in combination with features from other embodiments, including those discussed above.

According to an advantageous embodiment, the closure piece can be designed as a screw-type closure piece and/or as a snap-fit closure piece with at least one snap-in hook. This allows the sample-receiving chamber to be easily closed, in particular using one hand.

Alternatively or in addition, according to a further advantageous embodiment, provision can be made that the closure piece has a cover with a side wall, wherein an inner circumference of the side wall bears at least partially on an outer circumference of the outer wall, and/or the closure piece has a cover with a side wall partially protruding axially over an or the outer wall of the sample-receiving chamber. Even better closure of the sample-receiving chamber is thus made possible, preferably since the side wall portion of the cover protruding axially over the outer wall of the sample-receiving chamber can be provided to receive and/or form a sealing element. For example, at least one seal can be formed and/or arranged at the inner circumference of the side wall of the cover and/or at the outer circumference of the outer wall.

According to a further advantageous embodiment, the at least one seal can be designed as at least one axial seal and/or as at least one radial seal. The sample-receiving chamber can thus be sealed off particularly securely. For example, the at least one seal can be designed in such a way that, during the closing of the closure piece, the sample container can be closed in an airtight manner by a first seal, in particular an axial seal and/or a radial seal, and/or that the seal self-reinforcing as the internal pressure increases is designed as a second seal, in particular as an axial seal and/or as a radial seal.

To be able to prevent the sample container from being opened after said sample container has already been correctly closed, the closure piece of the sample container can be designed as a safety closure piece, by means of which the sample-receiving chamber is irreversibly closable, in particular such that, when used properly, the sample-receiving chamber is no longer openable after the closure.

To allow a user to determine whether the sample container has been properly closed, such that there is no possibility of contamination by substances escaping from an incorrectly closed sample-receiving chamber, the sample container can have a safety means by which, after the closure, a haptic and/or visual feedback is provided for a user, such that the user detects when closure has been carried out properly. The user thus also detects when the sample-receiving chamber is not fully closed by means of the closure piece. Therefore, the user will further process a sample contained in the sample container only when the safety means indicates that the sample-receiving chamber is properly closed. Moreover, the user can tell from the safety means whether it is safe for him, and for other persons around him, to leave a laboratory environment together with the sample container, for example in order to facilitate further processing, in particular by untrained personnel, outside the laboratory. Moreover, by virtue of the safety means, it is additionally possible to ensure that the sample in the sample-receiving chamber is not subsequently contaminated, which would distort an analysis result.

To make sample distribution inside the sample-receiving chamber easier, the compartments connected by liquid in the position of use can be formed by compartment walls projecting from a base of the sample-receiving chamber. Preferably, the compartment walls, measured from the base, can have a smaller height than at least one wall delimiting the sample-receiving chamber. It is thus possible that one sample introduced into one compartment of the sample-receiving chamber is sufficient to then distribute the sample material of the sample into at least one further compartment. The handling of the sample is made easier since, after closure of the sample-receiving chamber, a simple movement, e.g. shaking and/or swinging, suffices to distribute the sample material of the sample as uniformly as possible in the compartments.

In order to ensure that the compartments are thermally decoupled from each other completely or almost completely, the compartment walls can be arranged spaced apart from each other and/or do not touch each other.

To be able to perform an analysis of a sample contained in a compartment, for example by means of an auxiliary container, it may be advantageous if at least one compartment, in particular each compartment, has an assigned coupling point. Alternatively or in addition to this, at least one compartment, in particular each compartment, can have a predetermined breaking point. This has the advantage that the samples contained in different compartments can be tested independently of each other.

According to a further advantageous embodiment, provision can be made that the at least one predetermined breaking point is oriented in the radial and/or axial direction, and/or that the at least one predetermined breaking point is pierced through in the radial and/or axial direction during coupling of the sample container to an auxiliary container. In this context, an orientation in a defined direction can signify that a normal vector on a surface points in this direction.

According to a particularly advantageous embodiment, the at least one seal self-reinforcing as the internal pressure increases can be formed by an outer wall region of the sample-receiving chamber tapering in the direction of a container opening, in particular wherein a wall thickness of the outer wall region decreases, in particular decreases continuously, in the direction of the container opening. For example, the outer wall region can deform in the closed position, preferably if an internal pressure threshold value is reached, and/or if the outer wall region is displaced by closing of the sample-receiving chamber with the cover.

Alternatively or in addition to this, provision can be made, in a further advantageous embodiment, that the at least one seal self-reinforcing as the internal pressure increases is formed by a material recess, which is formed on an outer circumference of an outer wall, for example the aforementioned outer wall, of the sample-receiving chamber, and by a side wall of a cover, for example of the aforementioned cover, extending axially above the outer wall of the sample-receiving chamber. Preferably, an inner circumference of the side wall is supported on the outer circumference of the outer wall via at least one contact point, in particular a web. The at least one contact point can additionally act as or be configured as a sealing element, in particular as a radially and/or axially acting sealing means. For example, the at least one contact point can be formed at the outer circumference of the outer wall and/or at the inner circumference of the side wall of the cover.

According to a further advantageous embodiment, the at least one seal self-reinforcing as the internal pressure increases can be formed by an annular snap-fit connector. Particularly secure sealing is thus possible even at particularly high pressures.

The invention further relates to a use of the sample container as described and claimed herein, for cultivating and/or for analysis, in particular for chemical analysis, of a sample, wherein a liquid, in particular a nutrient medium, is introduced into the sample-receiving chamber, and a sample is arranged in at least one compartment of a sample-receiving chamber. As has already been described in relation to the sample container, a distribution of the sample material in the compartments is made possible by simple movements of the whole sample container, for example swinging and/or shaking movements. The sample container can remain closed in the process. Moreover, it is not necessary for every compartment to be charged individually with the sample material. Handling is thus made much easier.

According to an advantageous embodiment, provision can be made that the liquid and/or the sample is heated, in particular sequentially heated, in one of the compartments. In particular, a temperature of the liquid and/or of the samples in at least one other compartment, particularly in all further compartments, can remain unchanged or almost unchanged. Sequential heating can mean that the samples contained in different compartments can be subjected to different thermal treatments. For example, thermal treatment can be carried out by infrared radiation preferably with infrared heating. This has the advantage that different analysis methods can be carried out with the samples contained in different compartments.

As has already been mentioned above, provision can be made, according to an advantageous development, that by way of the liquid, in particular the liquid flowing over the compartment walls, the sample is distributed, in particular uniformly distributed, from one compartment into at least one further compartment, in particular by means of the sample container being shaken and/or swung around.

In order to permit particularly good distribution of sample material, introduced into one compartment or an interspace between the compartments, into the other compartments, provision can be made, in an advantageous embodiment, that a liquid, in particular a nutrient medium, is introduced into the sample-receiving chamber such that an upper edge of the compartment walls in each case lies below a liquid level.

The invention thus relates in particular to a sample container with a sample-receiving chamber and with a closure piece for closing the sample-receiving chamber in a sealed manner, wherein the sample container has at least two seals arranged separately from each other, and/or wherein the sample-receiving chamber is subdivided into at least two compartments which are thermally decoupled from each other and are connectable by liquid, and/or wherein the sample container has, on an outer wall of the sample-receiving chamber, at least one coupling point at which an auxiliary container is docked via a matching counter-coupling point of the auxiliary container, wherein the outer wall has at least one predetermined breaking point, which is pierced through upon coupling to the auxiliary container.

BRIEF DESCRIPTION OF THE DRAWINGS

The invention will now be described in more detail on the basis of a number of illustrative embodiments, although it is not restricted to these illustrative embodiments. Further illustrative embodiments arise by combining the features of individual claims or of a plurality of claims amongst themselves and/or with individual features or a plurality of features of the illustrative embodiments.

FIG. 5 shows a perspective view of a possible embodiment of a sample container without closure piece;

FIG. 6 shows a perspective view of a longitudinal section of the embodiment of the sample container from FIG. 5, wherein the sample-receiving chamber is subdivided into four compartments thermally decoupled from each other;

FIG. 7 shows a plan view of the sample container from FIGS. 5 and 6;

FIG. 10 shows a sixth design variant of a sample container, wherein the sample container has a coupling point formed by a latching hook, a latch recess and/or an indentation in the outer wall, which is designed to be connected to a matching counter-coupling point of an auxiliary container, in order to connect the sample container to the auxiliary container in particular in an irreversible manner;

FIG. 11 shows the design variant from FIG. 10, wherein the outer wall of the sample container has a predetermined breaking point which is pierced through by a piercing element upon coupling of the sample container to the auxiliary container, such that a liquid connection is established between the sample-receiving chamber and the auxiliary container;

DETAILED DESCRIPTION

Figure 1:
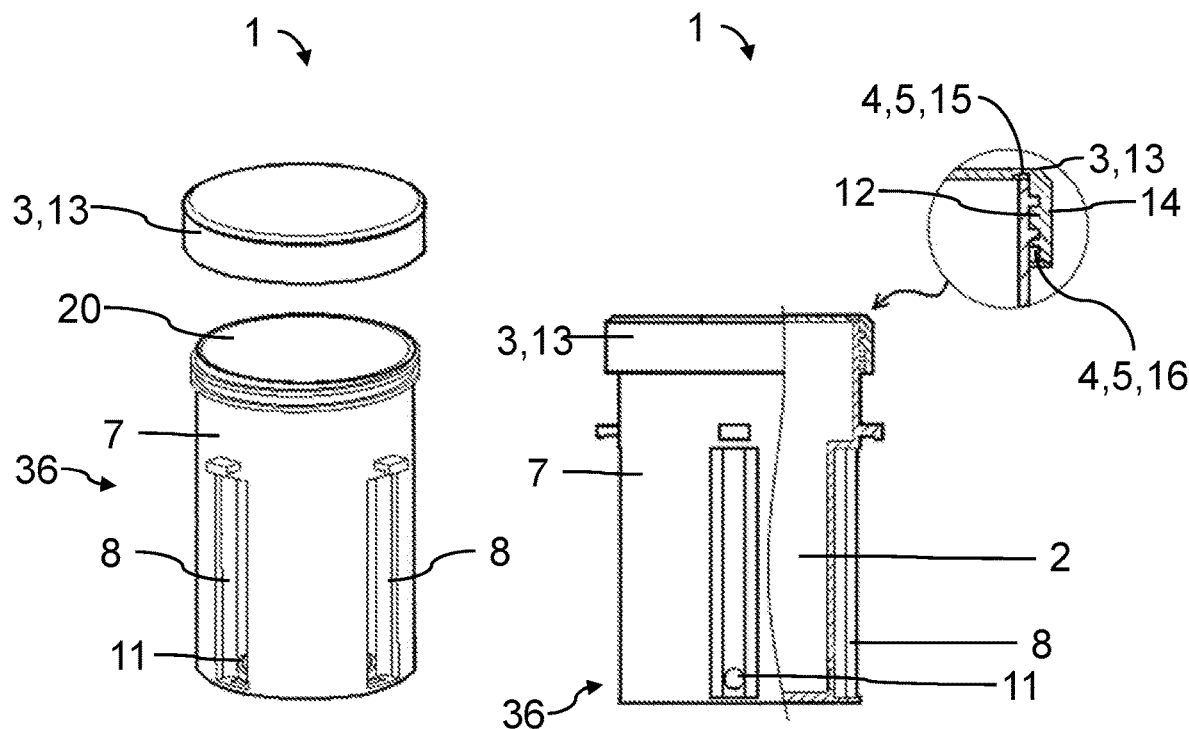
FIG. 1 shows a first design variant of a sample container according to the invention, with a first seal and a second seal in a perspective view and in a partially sectioned side view, wherein an irreversible latch connection is established between a closure piece, configured as a cover, and an outer wall region by means of at least one snap-in hook, such that the closure piece is no longer openable after it has been properly closed.

Several possible design variants of a sample container according to the invention, which is designated overall by reference number 1, are shown in FIGS. 1 to 13.

In the design variants shown, the sample container 1 is formed in at least two parts and has a sample-receiving chamber 2 and a closure piece 3 designed as a cover 13 for closing the sample-receiving chamber 2. However, it is also possible that the closure piece 3 is connected inseparably to the sample-receiving chamber 2. The cover 13 has a peripheral side wall 14 which, in the closed position, partially overlaps an outer wall 7 of the sample-receiving chamber 2, in particular in the axial direction.

The sample-receiving chamber 2 can be configured as a beaker 36, for example. The beaker 36 can here have a cylindrical shape in particular. The beaker 36 can in particular be stiff.

To close the sample-receiving chamber 2, the sample container 1 has for example a screw-type closure piece, which has an inner thread that cooperates with an outer thread on an outer wall 9 of the sample-receiving chamber 2.

Alternatively or in addition to this, the sample container 1 can have a snap-fit closure piece, i.e. in particular a screw-type snap-fit closure piece. It is possible here to design the snap-fit closure piece in such a way that the sample-receiving chamber 2 can be closed by the closure piece 3 irreversibly, i.e. cannot be opened. The snap-fit closure piece can, for example, have on the cover 13 one or more snap-in hooks 12 which engage in a recess or several recesses in the outer wall 7 and/or engage behind a projection on the outer wall 7. However, it is also conceivable that the principle described is reversed, such that the one or more snap-in hooks 12 are formed alternatively or in addition on the outer wall 7.

FIGS. 1-4 show a number of design variants of a sample container 1 having at least one seal 4, 5, 15, 16 which self-reinforces as the internal pressure increases. By interaction of the closure piece 3 with the outer wall 7 of the sample-receiving chamber 2, these are pressed more strongly onto each other axially and/or radially, at least at one contact point 23 and/or via a sealing means 23, as the internal pressure increases. The contact point 23 can be, for example, a contact face and/or a contact line, preferably a circumferentially extending contact face.

The seals 4, 5, 15, 16 can each be formed by molded material on the outer wall 7 and/or on the closure piece 3 and/or by deformable sealing means 23 arranged between the closure piece 3 and the outer wall 7, for example sealing rings.

In the design variants of the sample container 1 shown in FIGS. 1-4, at least a first seal 4 and a second seal 5 are provided. The sample container 1 thus has a two-stage seal. By means of the first seal 4, the sample-receiving chamber 2 can already be sealed off in a liquid-tight manner by closure of the cover 13. By means of the second seal 5, it is finally possible to achieve even better sealing of the sample-receiving chamber 2, in particular a pressure-tight sealing. It is thus possible for a liquid-filled sample container 1 to be exposed to high temperatures, for example in an autoclaving process, without losing its leak-tightness.

In the examples shown, the first seal 4 is designed as a seal acting in the radial direction (radial seal 16). It can be formed for example by a sealing ring and/or by sealing means 23 that are molded on the outer wall 7 of the sample-receiving chamber 2. However, the first seal 4 can also be designed as a seal acting in the axial direction (axial seal 15).

In the examples shown, the second seal 5 is designed as a seal acting in the axial direction (axial seal 15). The axial seal 15 can be formed by a sealing element, for example a sealing ring, molded on an edge of the container opening 20. However, the second seal 5 can also be designed as a seal acting in the radial direction (radial seal 16).

Figure 2:
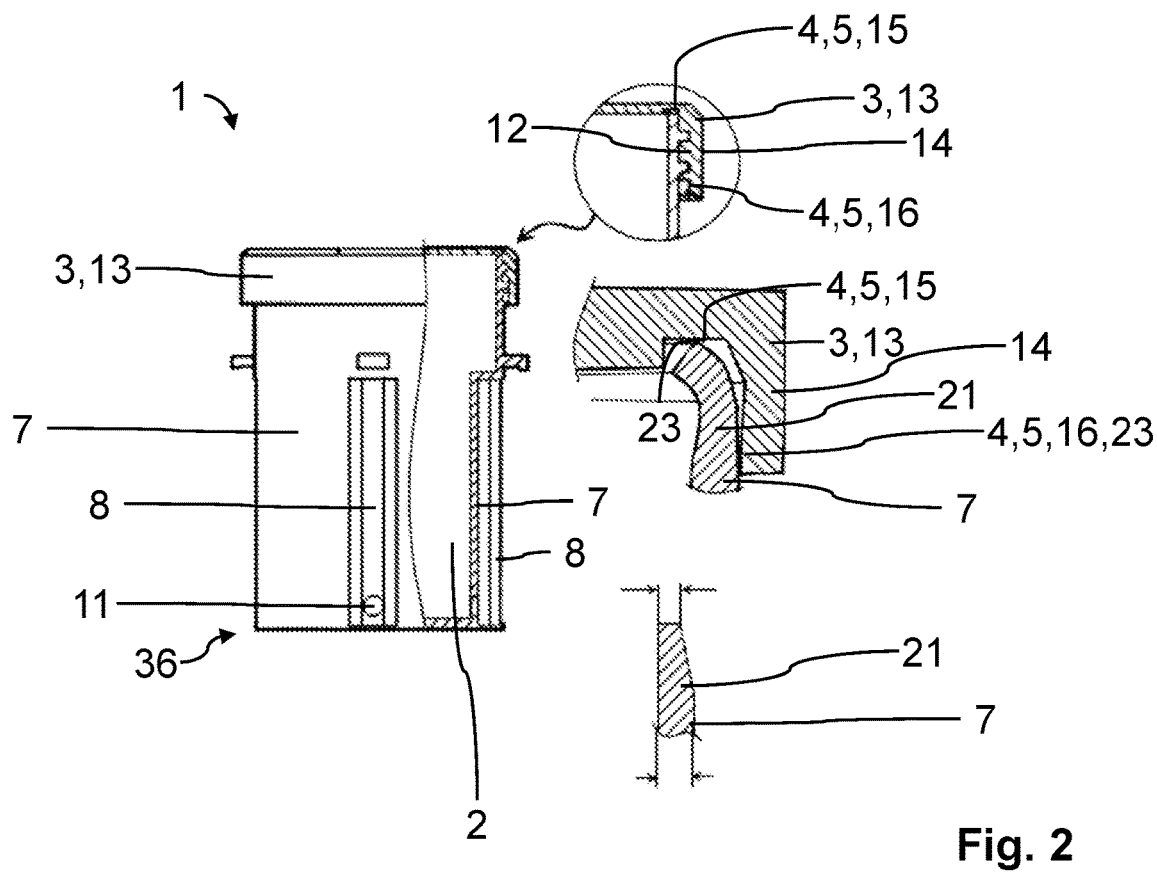
FIG. 2 shows a second design variant of a sample container according to the invention, wherein a wall thickness of an outer wall region decreases in the direction of a container opening and thus tapers in longitudinal section, wherein the outer wall region is at least in part deformed radially inward such that an edge region of the container opening, together with the cover, forms an axially acting seal (axial seal), and a side wall region of the cover forms via its inner circumference a radially acting seal (radial seal) with an outer circumference of an outer wall of the sample container.

FIG. 2 shows a design variant of the sample container 1 whose outer wall 7 has a wall thickness decreasing in the direction of the container opening 20, i.e. it has an outer wall region 21 tapering, in particular tapering continuously, in longitudinal section. A predetermined bending point can be formed by the reduction of the wall thickness. The two seals 4, 5, 15, 16 are formed here by a deformation of the outer wall region 21 of the sample-receiving chamber 2 in the radial direction, preferably by an inward bending of the outer wall region 21. Alternatively or in addition, the deformation of the outer wall region 21 can be effected at least partially by an internal pressure in the interior of the sample-receiving chamber 2 acting on the cover 13 and on the outer wall region 21. Alternatively or in addition, an initial deformation may occur when the sample-receiving chamber 2 is closed with the cover 13, in particular screwed shut (even if there is no increased pressure in the interior).

By means of the deformation, at least two contact points/sealing means 23 can be formed between the cover 13 and the outer wall 7. An edge region of the container opening 20, formed by the outer wall 7, is deformed such it touches the cover 13 only with one edge face and thereby forms a sealing means 23 and/or a contact point 23. An axial seal 15 is thus formed here.

A further contact point and/or a further sealing means 23 is formed between the outer circumference of the outer wall 7 and the inner circumference of a side wall 14 of the cover 13. A radial seal 16 is thus formed.

If the internal pressure increases, the cover 13 and the outer wall 7 are pressed more strongly against each other at least in the at least two contact points. This principle of action is implemented also in the design variants from FIGS. 3 and 4, wherein the respective structural embodiment differs. However, it is possible to combine the features of the design variants of FIGS. 2 to 4 with one another in order to form a new design variant.

Figure 3:
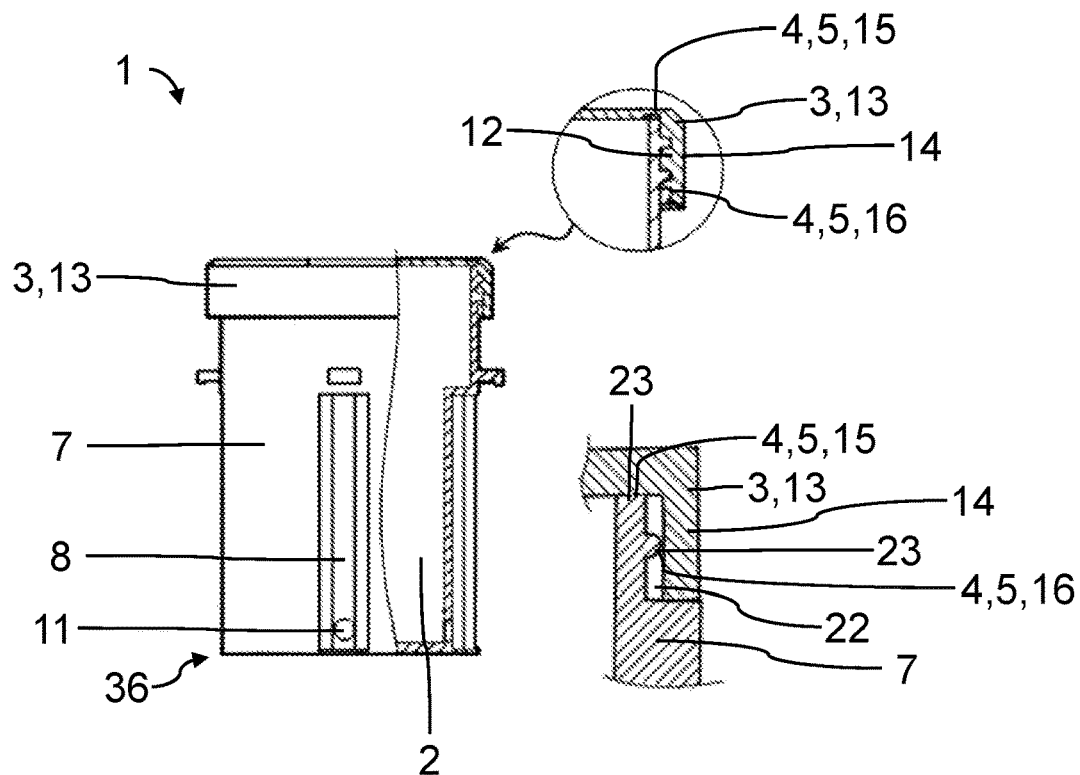
FIG. 3 shows a third design variant of a sample container according to the invention, wherein a wall thickness of an outer wall region decreases in the direction of a container opening and thus tapers in longitudinal section, wherein an edge region of the container opening, together with the cover, forms an axially acting seal (axial seal), and a side wall region of the cover forms via its inner circumference a radially acting seal (radial seal) with an outer circumference of an outer wall of the sample container, wherein the outer wall region and/or the cover have/has at least one sealing means via which at least one contact point with the side wall of the cover is produced in the closed position.

FIG. 3 shows a design variant of the sample container 1 whose outer wall 7 has a wall thickness decreasing in the direction of the container opening 20, in particular with a step. The material recess 22 can be configured, for example, as a circumferentially extending groove. At the outer circumference of the outer wall 7, a preferably web-shaped and/or peripheral sealing means 23 is formed, via which a contact point 23 with the side wall 14 of the cover 13 is produced in the closed position. A radial seal 16 is thus formed.

The edge region of the container opening 20 forms, together with the cover 13, at least one further contact point 23. A sealing means forming at the at least one further contact point 23 can be formed, in particular integrally molded, and/or arranged on the cover 13 and/or on the edge of the container opening 20. An axial seal 15 is thus formed.

If the internal pressure in the sample-receiving chamber 2 increases, a deformation of the outer wall 7 also takes place here, as a result of which the seals 4, 5, 15, 16 self-reinforce, by means of the contact pressure between the outer wall 7 and the cover 13, and/or between the edge, in particular an end face, of the container opening 20 and the cover 13, increasing at least at the contact points 23.

Figure 4:
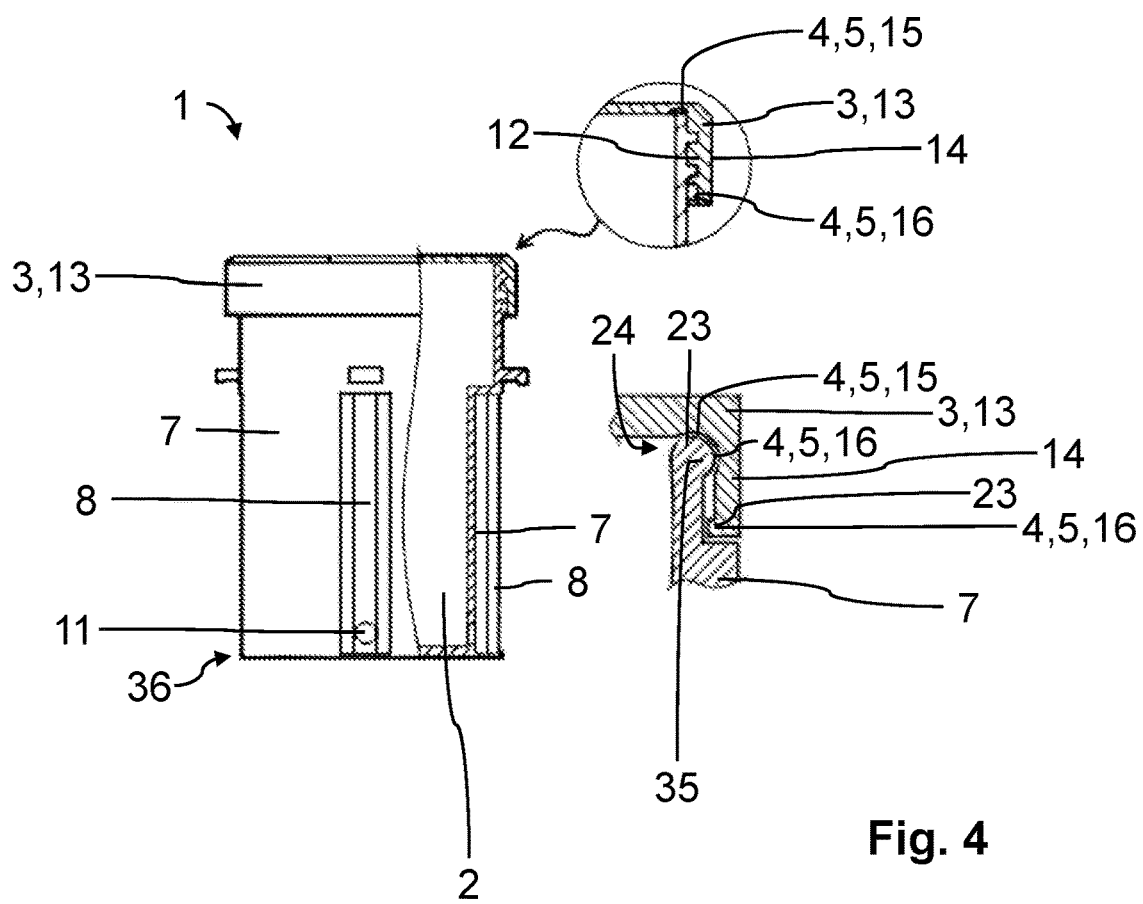
FIG. 4 shows a fourth design variant of a sample container according to the invention, wherein a wall thickness of an outer wall region firstly decreases in the direction of a container opening and then increases again at a bead, wherein an edge region of the container opening, together with the cover, forms an axially acting seal (axial seal), and a side wall region of the cover forms via its inner circumference a radially acting seal (radial seal) with an outer circumference of an outer wall of the sample container, wherein the outer wall region and/or the cover have/has at least one sealing means via which at least one contact point with the side wall of the cover is produced in the closed position.
Figure 8:
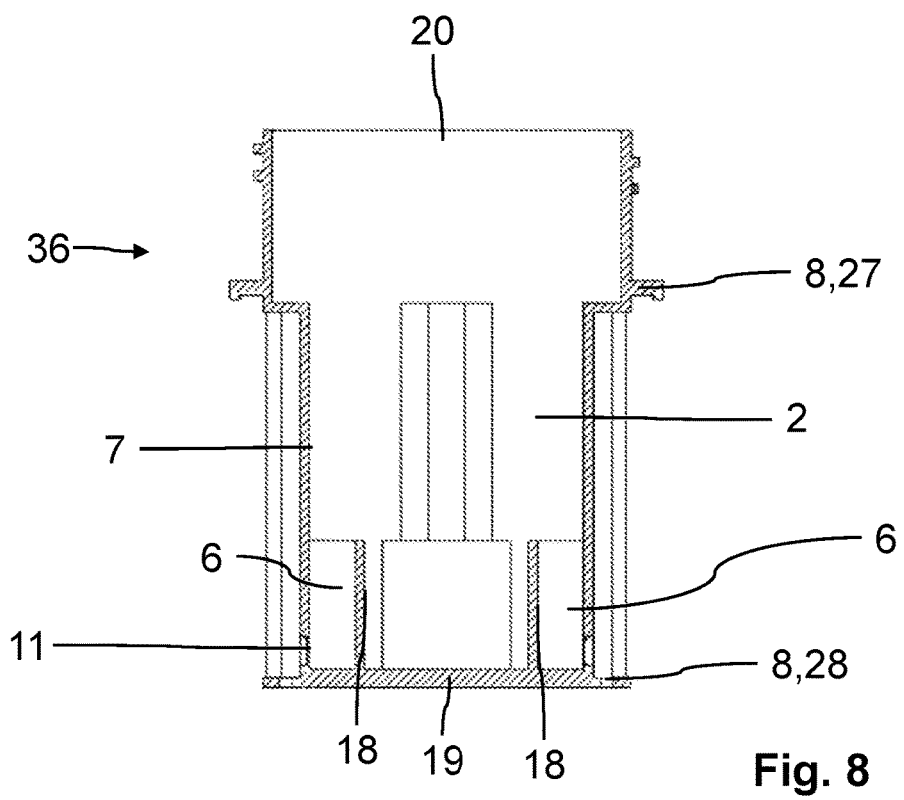
FIG. 8 shows a side view of a longitudinal section of the embodiment of the sample container from FIGS. 5-7, wherein the sample-receiving chamber is subdivided into four compartments thermally decoupled from each other.

FIG. 4 shows a further design variant of a sample container 1, which has a closure piece 3 with an annular snap-fit connector 24. At the edge of the container opening 20, a sealing means 23 configured as a bead 35 is formed which, in the closed position of the sample container 1, forms at least one contact point 23, preferably at least one axially acting and/or radially acting contact point 23, with the cover 13.

The cover 13, in particular the above-described annular snap-fit connector 24, has, at the edge region of the side wall 14 of the cover 13, a radially outwardly directed projection which, in the closed position, engages in a corresponding recess in the outer wall 7 and forms a preferably irreversible latching connection. A (further) radial seal 16 is thus formed here. At the same time, the cover 13 and the beaker 36 can be connected to each other inseparably by the resulting latching connection. Therefore, by means of the latching connection formed in the closed position of the sample container 1, the sample-receiving chamber 2 can no longer be opened when used as intended.

The sample container 1 shown in FIGS. 5-9 has a sample-receiving chamber 2 subdivided into four compartments 6, wherein the compartments 6 are thermally insulated from each other by an interspace (free space) in the middle of the sample-receiving chamber 2.

Figure 9:
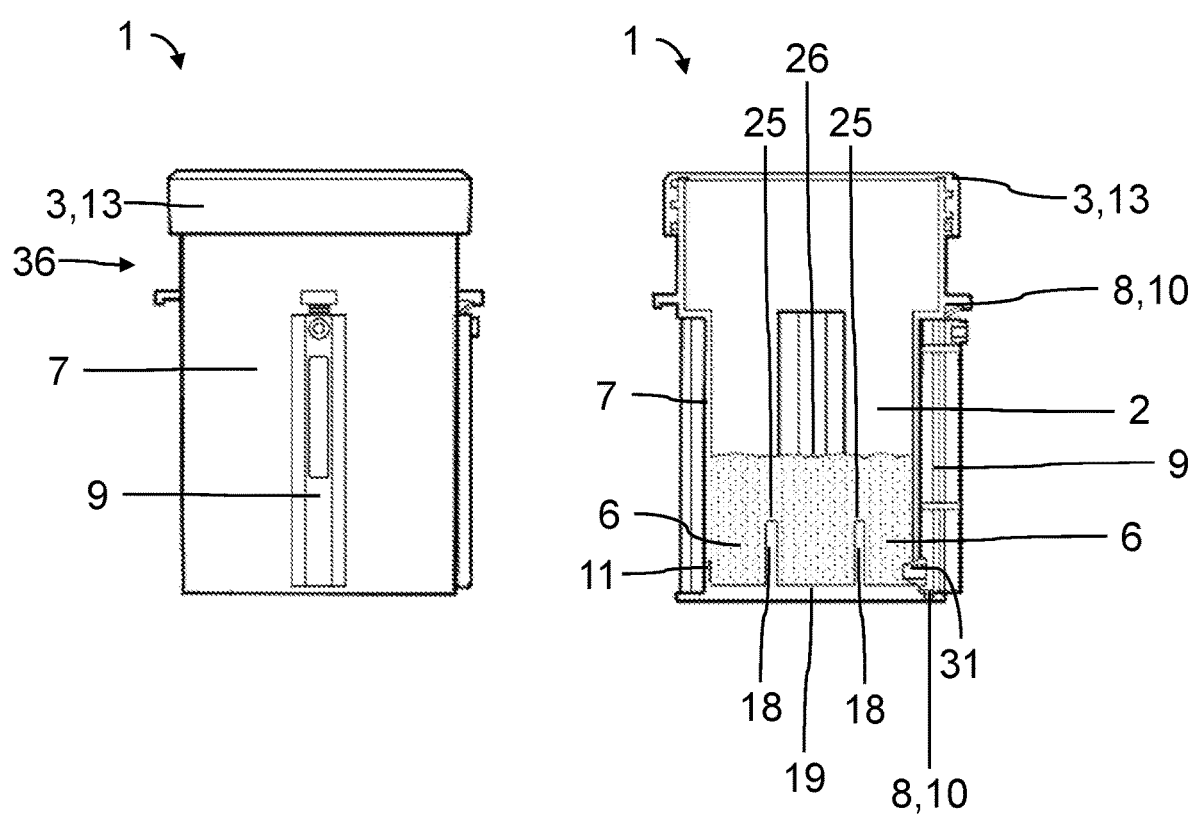
FIG. 9 shows a fifth design variant of a sample container which is configured for sequential heating of its compartments, by means of the latter being spatially separated from each other inside the sample-receiving chamber, wherein a liquid level, during the use of the sample container, inside the sample-receiving chamber is higher than an upper edge of the compartment walls.

As is shown in FIG. 9, provision is made that when the sample-receiving chamber 2 is filled as intended with a liquid, e.g. a nutrient medium, a liquid level 26 measured from a base 19 of the sample-receiving chamber 2 lies above an edge 25 of the compartment walls 18. The compartment walls 18 here form, together with the outer wall 7, the individual compartments 6. Thus, during use, the compartments 6 are connected to each other via the liquid.

Measured from the base 19, the outer wall 7 delimiting the sample-receiving chamber 2 is higher than the individual compartment walls 18. An overflowing of the individual compartments 6 is thus possible. This has the advantage that a sample only has to be introduced into one compartment 6, after which the sample container 1 can be closed, and, by swinging and/or shaking the sample container 1, an almost uniform distribution of the sample material in all compartments 6 is possible. This simplifies handling, particularly when dealing with toxic or infectious samples.

Due to the thermal decoupling of the compartments 6, it is possible for samples contained therein to be heated independently of each other. The heating can be effected here, for example, by infrared heating. Thus, different culture conditions and/or reaction conditions can be created inside a sample-receiving chamber 2.

Each compartment 6 has a predetermined breaking point 11 lying inside the compartment 6 and formed by an outer wall 7. The predetermined breaking points 11 serve to permit liquid exchange between an auxiliary container 9 that can be coupled to the sample container 1. Design variants of this are shown in FIGS. 10 and 11. Sample container 1 and auxiliary container 9 can together form a set for cultivation and analysis of a sample.

The sample container 1 has a coupling point 8 for each predetermined breaking point 11. As is shown in FIGS. 5, 6 and 7, the coupling point 8 can be formed, for example, by a latching hook 27 and a latch recess 28. By means of the coupling point 8, the sample container 1 can thus be coupled to the auxiliary container 9 via a suitable counter-coupling point 10. The coupling point 8 can moreover have a receiving bay formed on the outer wall 7 for the auxiliary container 9. The counter-coupling point 10 can be formed, for example, by a latching lug 29, which engages in the latch recess 28 in the closed position, and a spring element 30, which is acted upon by the latching hook 27 in the closed position.

The auxiliary container 9 can thus be plugged via the latching lug 29 into the latch recess 28 formed in the base 19. A rotation axis can thus be formed by the latching lug 29 and the latch recess 28. The auxiliary container 9 can then be inserted in the radial direction into the predetermined breaking point 11 via a piercing element 31. In this way, the predetermined breaking point 11 is punctured by the piercing element 31, such that a liquid connection between the auxiliary container 9 and the sample-receiving chamber 2 is produced. The described embodiment has the advantage of achieving the greatest possible lever action, such that the piercing of the predetermined breaking point 11 is possible with relatively little force being applied, since the upper end of the auxiliary container is guided in a circular movement in the direction of the outer wall 7 until the latching hook 27 latches onto the spring element 30.

The spring element 30 can be formed, for example, as an obliquely protruding, pretensioned wing through which a spring force is generated, which has to be overcome when the latching hook 27 is latched onto the spring element 30.

Figure 12:
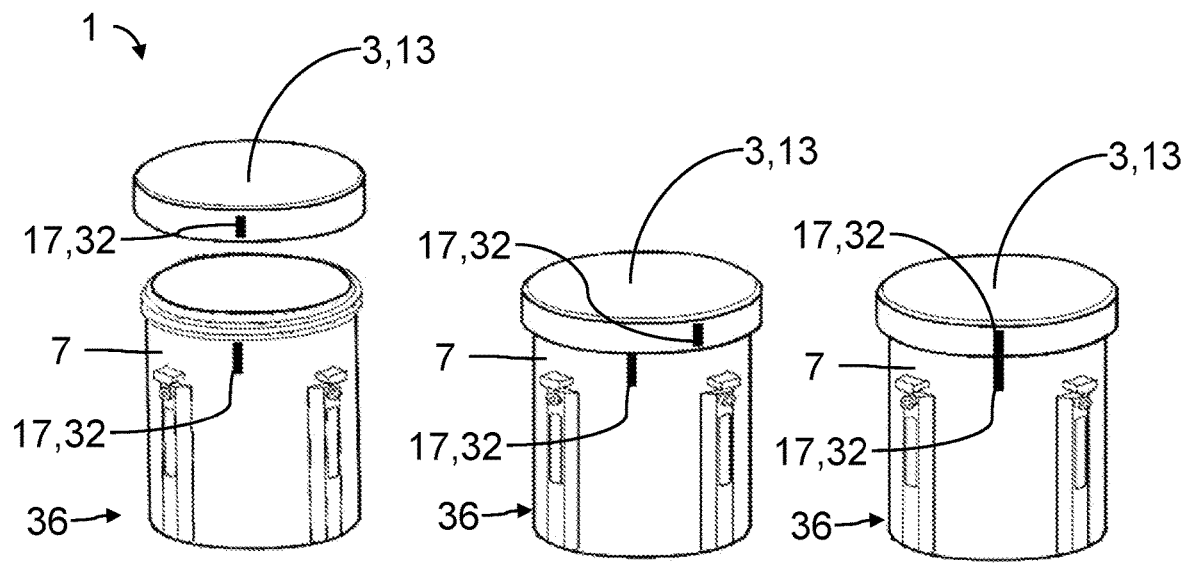
FIG. 12 shows a seventh design variant of a sample container, wherein a safety means in the form of markings is present at the closure piece and at the outer wall of the sample-receiving chamber, wherein the two markings are arranged in alignment with each other when the sample-receiving chamber is properly closed.
Figure 13:
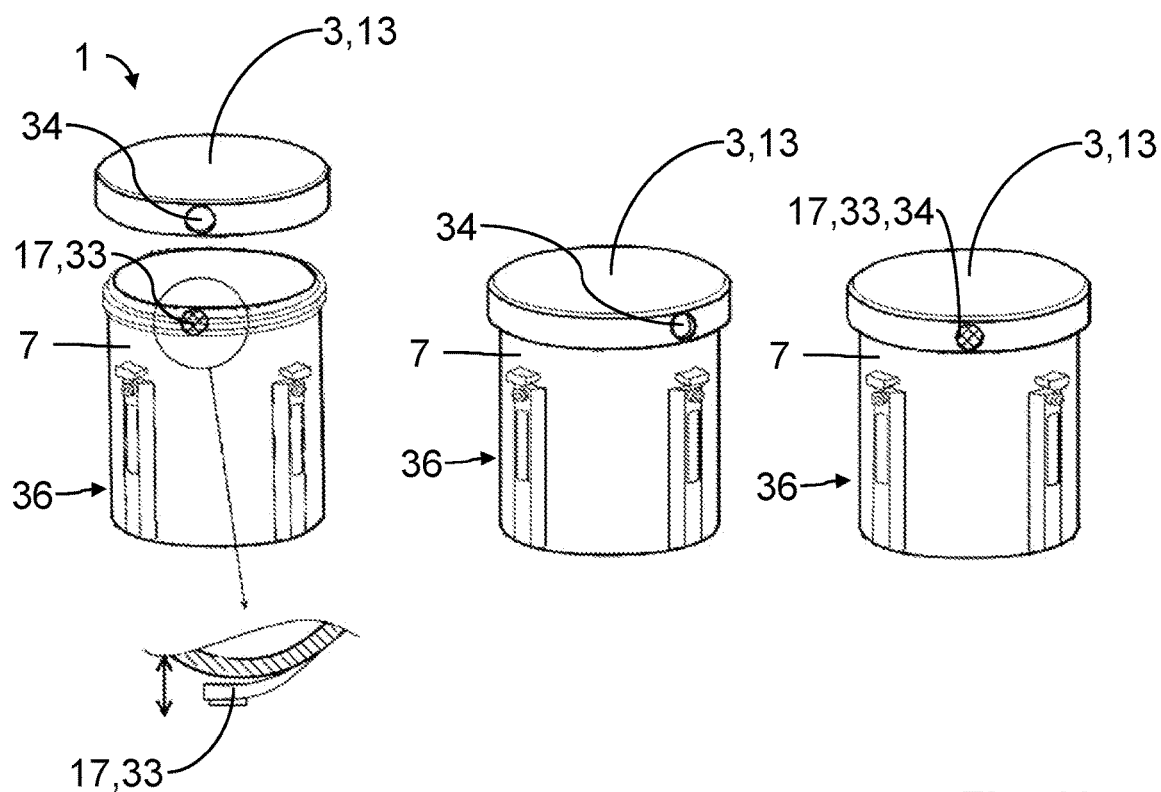
FIG. 13 shows an eighth design variant of a sample container, wherein the closure piece has a hole which, only when the sample-receiving chamber has been properly closed, allows a view of a visible closure element at the outer wall.

FIGS. 12 and 13 show a design variant of a sample container 1 having a safety means 17 which, after the beaker 36 has been closed with the cover 13, allows a user to ascertain whether the sample-receiving chamber 2 is closed properly, i.e. in particular in a sealed manner. By virtue of the safety means 17, the user can tell by touch and/or by sight whether the sample container 1 is properly closed.

FIG. 12 shows a design variant in which a marking in the form of a line, in particular a vertical line, is applied in particular to the outer face of the side wall 14. On its outer face, the beaker 36 likewise has a lined marking. When the beaker 36 is closed with the cover 13, for example by a screw connection and/or a snap-fit connection, the cover 13 is rotated relative to the beaker 36 until the two markings lie over each other, i.e. are arranged in alignment with each other. The safety means 17 in the form of markings thus allows a visual recognition of the fact that the closure has been carried out properly.

FIG. 13 shows a supplementary or alternative design variant in relation to the preceding one. In its side wall 14, the cover 13 has a hole 34 which functions similarly to the principle of the above-described line markings. The cover 13 is rotated relative to the beaker 36 until, in the closed position, the hole 34 is arranged over a marking 32, for example a closure element 33 that becomes visible. The user can thus see the closure element 33 only when the sample-receiving chamber 2 has been closed properly. At the same time, the closure element 33 can be configured such that, as an alternative or addition to the visual recognition, a haptic and/or tactile recognition obtained by feeling the closure element 33 is possible only when the sample-receiving chamber 2 has been closed properly. By closing the sample-receiving chamber 2 with the closure piece 3, the closure element 33 can be adjusted from a first position to a second position. The closure element 33 can here be configured in such a way that it can be felt and/or seen by the user in one of the two positions.

LIST OF REFERENCE SIGNS 1 sample container
2 sample-receiving chamber
3 closure piece
4 first seal
5 second seal
6 compartment
7 outer wall
8 coupling point
9 auxiliary container
10 counter-coupling point
11 predetermined breaking point
12 snap-in hook
13 cover
14 side wall
15 axial seal
16 radial seal
17 safety means
18 compartment wall
19 base
20 container opening
21 tapering outer wall region
22 material recess
23 contact point/sealing means
24 annular snap-fit connector
25 upper edge of the compartment wall
26 liquid level
27 latching hook
28 latch recess
29 latching lug
30 spring element
31 piercing element
32 marking
33 closure element becoming visible
34 hole
35 bead
36 beaker

The invention claimed is:

1. A sample container (1), comprising:
a sample-receiving chamber (2),
a closure piece (3) for closing the sample-receiving chamber (2), and
at least one seal (4, 5, 15, 16) which self-reinforces as an internal pressure increases, wherein the sample-receiving chamber (2) is closeable in an airtight manner by the closure piece (3).

2. The sample container (1) as claimed in claim 1, wherein:
the sample-receiving chamber (2) is subdivided into at least two compartments (6) which are thermally decoupled from each other and are connectable by liquid or which, in a position of use, are connected by liquid.

3. The sample container (1) as claimed in claim 1, wherein:
the sample-receiving chamber (2) includes an outer wall (7)
with at least one coupling point (8) on the outer wall (7), at which, in order to permit a liquid transfer, an auxiliary container (9) is docked via a matching counter-coupling point (10), the at least one coupling point comprises at least one predetermined breaking point (11), which is configured to be pierced through upon coupling to the auxiliary container (9).

4. The sample container (1) as claimed in claim 1, wherein the closure piece (3) comprises at least one of a screw-type closure piece, a snap-fit closure piece with at least one snap-in hook (12), or a cover (13) with a side wall (14) having an inner circumference that bears at least partially on an outer circumference of the outer wall (7).

5. The sample container (1) as claimed in claim 1, wherein the at least one seal (4, 5, 15, 16) comprises at least one of an axial seal (15) or a radial seal (16), and during the closing of the closure piece (3), the sample container (1) is closeable in an airtight manner by a first one of the seals (4), and the seal (4, 15, 16) is self-reinforcing as the internal pressure increases via a second one of the seals (5).

6. The sample container (1) as claimed in claim 1, wherein the closure piece (3) of the sample container (1) comprises a safety closure piece, by which the sample-receiving chamber (2) is irreversibly closable.

7. The sample container (1) as claimed in claim 1, wherein the sample container (1) has a safety indicator (17) by which, after closing, provides at least one of a haptic or visual feedback for a user, such that the user detects that the closure has been carried out properly.

8. The sample container (1) as claimed in claim 2, wherein the compartments (6) connected by liquid in a position of use are formed by compartment walls (18) projecting from a base (19) of the sample-receiving chamber (2), and the compartment walls (18), measured from the base (19), have a smaller height than at least one wall (7) delimiting the sample-receiving chamber (2).

9. The sample container (1) as claimed in claim 8, wherein the compartment walls (18) are arranged at least one of spaced apart from each other or do not touch each other.

10. The sample container (1) as claimed in claim 1, wherein at least one of the compartments (6) has at least one of an assigned coupling point (8) or a predetermined breaking point (11).

11. The sample container (1) as claimed in claim 10, wherein the at least one predetermined breaking point (11) is oriented in at least one of a radial or axial direction, and the at least one predetermined breaking point (11) is pierced through in the a least one of the radial or axial direction during coupling of the sample container (1) to an auxiliary container (9).

12. The sample container (1) as claimed in claim 1, wherein the at least one seal (4, 5, 15, 16) that is configured as self-reinforcing as the internal pressure increases is formed by an outer wall region (21) of the sample-receiving chamber (2) tapering in a direction of a container opening (20), in particular wherein the outer wall region deforms in the closed position.

13. The sample container (1) as claimed in claim 1, wherein the at least one seal (4, 5, 15, 16) that is self-reinforcing as the internal pressure increases is formed by a material recess (22) formed on an outer circumference of an outer wall (7) of the sample-receiving chamber (2), and by a side wall (14) of a cover (13) that forms the closure piece, and an inner circumference of the side wall is supported on the outer circumference of the outer wall (7) via at least one contact point (23).

14. The sample container (1) as claimed in claim 1, wherein the at least one seal (4, 5, 15, 16) that is self-reinforcing as the internal pressure increases is formed by an annular snap-fit connector (24).

15. A method for at least one of cultivating or for analysis of a sample using the sample container (1) as claimed in claim 2, comprising
introducing a liquid into the sample-receiving chamber (2),
arranging a sample in at least one compartment (6) of the sample-receiving chamber (2); and
heating at least one of the liquid or the sample in one of the compartments (6), while a temperature of the other of the liquid or of the sample in at least one other compartment (6) remains substantially unchanged.

16. The method as claimed in claim 15, wherein the liquid is a nutrient medium that is introduced into the sample-receiving chamber (2), such that an upper edge (25) of the compartment walls (18) of the compartments (6) in each case lies below a liquid level (26).

17. The method as claimed in claim 15, further comprising distributing the liquid by the liquid flowing over the compartment walls (18) from one of the compartments (6) into at least one further one of the compartments (6) by at least one of shaking or swinging around the sample container (1).

* * * * *